US011049241B2

United States Patent
Yu et al.

(10) Patent No.: US 11,049,241 B2
(45) Date of Patent: Jun. 29, 2021

(54) QUALIFICATION METHOD OF LUNG VESSEL BASED ON LOBE

(71) Applicants: Coreline Soft Co., Ltd., Seoul (KR); The Asan Foundation, Seoul (KR); UNIVERSITY OF ULSAN FOUNDATION FOR INDUSTRY COOPERATION, Ulsan (KR)

(72) Inventors: Donghoon Yu, Seoul (KR); Hyungi Seo, Seoul (KR); Joon Beom Seo, Seoul (KR); Nam Kug Kim, Seoul (KR)

(73) Assignees: Coreline Soft Co., Ltd., Seoul (KR); The Asan Foundation, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 13 days.

(21) Appl. No.: 16/430,971

(22) Filed: Jun. 4, 2019

(65) Prior Publication Data
US 2019/0370964 A1   Dec. 5, 2019

(30) Foreign Application Priority Data
Jun. 4, 2018  (KR) .................. 10-2018-0064258

(51) Int. Cl.
  *A61B 6/00*  (2006.01)
  *G06T 7/00*  (2017.01)
  *A61B 6/03*  (2006.01)
  *G06T 7/62*  (2017.01)
  *G06T 7/10*  (2017.01)

(52) U.S. Cl.
  CPC .............. *G06T 7/0012* (2013.01); *A61B 6/03* (2013.01); *G06T 7/62* (2017.01); *A61B 6/504* (2013.01); *A61B 6/52* (2013.01); *G06T 7/10* (2017.01); *G06T 2207/10081* (2013.01); *G06T 2207/30101* (2013.01)

(58) Field of Classification Search
  CPC .. A61B 6/03; A61B 6/52; A61B 6/504; A61B 6/5217; G06T 7/0012; G06T 7/62; G06T 7/10; G06T 7/00; G06T 7/155; G06T 2207/30101; G06T 2207/10081; G06T 15/08; G16H 50/30
  See application file for complete search history.

(56) References Cited

U.S. PATENT DOCUMENTS 7,206,462 B1 *  4/2007  Betke .................... G06T 7/0012
                                                           378/21
8,417,009 B2    4/2013  Mizuno
(Continued)

FOREIGN PATENT DOCUMENTS

| KR | 100999232 B1 | 12/2010 |
| KR | 101135205 B1 | 4/2012 |
| KR | 101511300 B1 | 4/2015 |

*Primary Examiner* — Matthew C Bella
*Assistant Examiner* — Kathleen M Broughton
(74) *Attorney, Agent, or Firm* — Nelson Mullins Riley & Scarborough LLP; Kongsik Kim, Esq.

(57) ABSTRACT

Disclosed is a method for the quantification of pulmonary vessels by lobe, the method including extracting, at extraction unit, pulmonary vessels based on a medical image, locating, at analysis unit, voxels of pulmonary vessels with respect to the surface of a lobe, and quantifying, at calculation unit, the extracted pulmonary vessels.

6 Claims, 13 Drawing Sheets initial boundary surface (56) References Cited

U.S. PATENT DOCUMENTS

| | | | |
|---|---|---|---|
| 9,996,918 B2 | 6/2018 | Kim et al. | |
| 2009/0185731 A1* | 7/2009 | Ray | G06T 7/12 |
| | | | 382/131 |
| 2011/0237938 A1* | 9/2011 | Mizuno | G06T 7/187 |
| | | | 600/425 |
| 2014/0105472 A1* | 4/2014 | Yin | A61B 5/08 |
| | | | 382/128 |
| 2015/0238270 A1* | 8/2015 | Raffy | A61B 5/7275 |
| | | | 600/407 |
| 2016/0189373 A1* | 6/2016 | Park | G06T 7/0012 |
| | | | 382/131 |

* cited by examiner

FIG. 1

Prior Art

FIG. 2A

Prior Art

FIG. 2B

Prior Art

FIG. 2C

Prior Art

FIG. 2D

Prior Art

FIG. 5 distance field generation

QUALIFICATION METHOD OF LUNG VESSEL BASED ON LOBE

CROSS REFERENCE TO RELATED APPLICATION

This application claims the benefit of and priority to Korean Patent Application No. 10-2018-0064258, filed on Jun. 4, 2018. The entire disclosure of the above application is incorporated herein by reference.

FIELD

The present disclosure is generally related to a method for the quantification of pulmonary blood vessels, and in particular, to a method for the quantification of pulmonary vessels by lobe.

BACKGROUND

This section provides background information related to the present disclosure which is not necessarily prior art.

FIG. 1 and FIG. 2(A) to FIG. 2(E) illustrate an exemplary method of the pulmonary vessel extraction for automatically detecting a lesion in a thoracic CT image, which is presented in registered Korean Patent Publication No. 10-2011-0129239.

Figure 1:
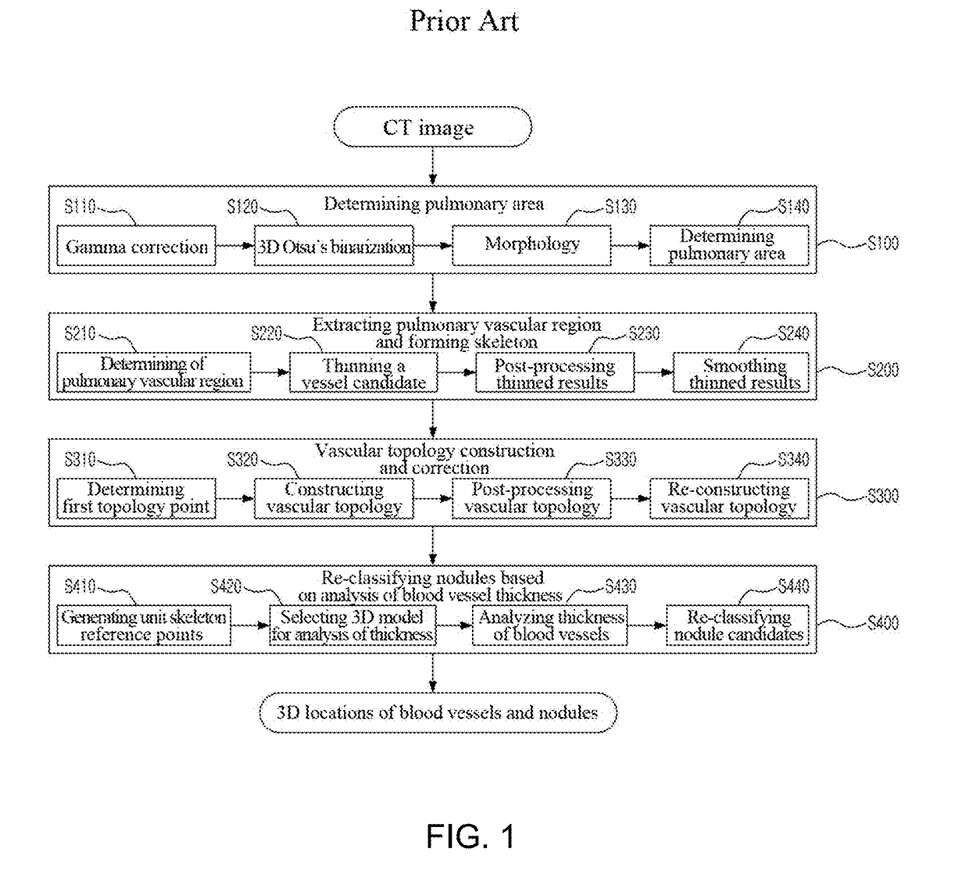
FIG. 1 and FIGS. 2A, 2B, 2C, 2D and 2E illustrate an exemplary method of the pulmonary vessel extraction for automatically detecting a lesion in a thoracic CT image, which is presented in registered Korean Patent Publication No. 10-2011-0129239.

FIG. 1 is a flow chart describing an exemplary embodiment of a method of extracting pulmonary vessels for automatic detection of a lesion in a thoracic CT image. As illustrated in the drawing, the method includes determining a pulmonary area (S100), extracting a pulmonary vascular region and forming a skeleton (S200), construct and correcting a vascular topology (S300), and analyzing thickness of blood vessels for nodular reclassification (S400).

In step S100, a target pulmonary area is determined in a thoracic CT image for extracting pulmonary vessels. Referring back to FIG. 1, this step S100 for determining a pulmonary area includes applying a gamma correction to an original thoracic CT image (S110), executing image binarization on the gamma corrected image (S120), performing a morphological operation on the binarized image (S130), and determining a vessel and a pulmonary area (which is a target of nodules) in the image where the morphological operation is performed (S140). Step S100 is discussed in further detail below.

In step S100 where a pulmonary area is determined, a thoracic CT image with a relatively low intensity attenuation ratio is corrected using Eq. 1, and converted to a binary image by Otsu's method for binarization:

$$LV_{new} = (LV_{old}/255)^{gamma} * 255 \qquad \text{Eq. 1.}$$

where a gamma value used for the correction was 1.7. A morphological operation is then performed on the binarized image to determine a vessel and a pulmonary area (which is a target of nodules) in the image.

In step S200, a pulmonary vascular region is first determined by executing image binarization on the original image data in the pulmonary area determined in step S100, and a skeleton line of the vessel is formed by a thinning process. As described in FIG. 1, this step S200 includes determining a pulmonary vascular region (S210), thinning a vessel candidate (S220), post-processing the thinned results (S230), and smoothing the thinned results (S240). In particular, the pulmonary area determined in step S100 is used as a target area in the extraction of a pulmonary vascular region for separating the vascular region from the normal lung tissues. This separation of the vascular region in the pulmonary area is done by utilizing the Otsu's method for binarization. Here, the original image data included in the pulmonary area is subjected to the Otsu's method and a threshold for determining a target vascular region is calculated such that cost for iterating the calculation of a threshold for separating a vascular region in the pulmonary area each time can be reduced, as in the case of thresholding the pulmonary area. Once the pulmonary vascular region is determined by binarizing the pulmonary area image with a threshold for determining the vascular region, a thinning process is carried out to form a skeleton line of the vessel. This thinning process is usually used for fingerprint recognition or online character recognition (OCR). In particular, skeleton lines of fingerprints or strokes of characters are obtained, and features of those skeleton lines are then used for identifying an individual or character. A skeleton line formed by thinning becomes the basis for measuring and analyzing thickness of the blood vessels.

In step S300, a vascular topology of skeleton lines is configured by separating data on the skeleton lines from S200 into skeleton line intersections and unit skeleton lines, and connecting them. Referring again to FIG. 1, this step S300 includes determining a first topology point (S310), constructing a vascular topology (S320), post-processing the vascular topology (S330), and re-constructing the vascular topology (S340). Next, in step S400, thickness of blood vessels is analyzed from the original data of the vascular region as well as from the vascular topology constructed in step S300, and nodule candidates are re-classified based on the analysis. Turning back to FIG. 1, this step S400 includes generating reference points that divide pixels of a skeleton line in the vascular topology from step S300 at regular intervals (S410), analyzing the thickness of blood vessels using the reference points thus generated (S430), and re-classifying nodule candidates based on the analyzed thickness of blood vessels (S440). Optionally, the step S400 may further include selecting a 3D model for the analysis of thickness of blood vessels (S420).

FIG. 2 illustrates an image conversion procedure following the flow of the step of determining a pulmonary area.

Figure 2A:
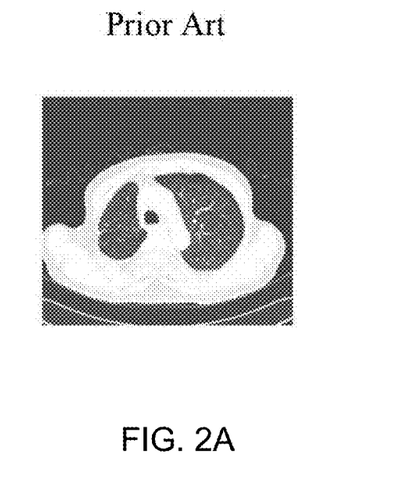
Figure 2B:
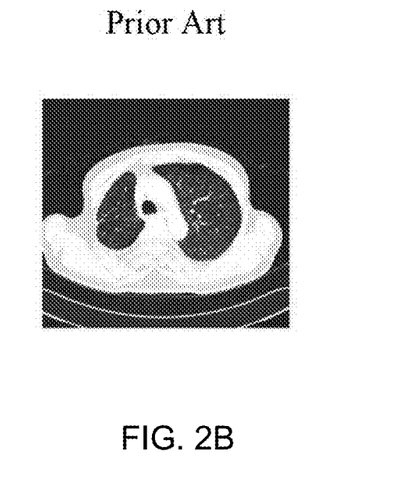
Figure 2C:
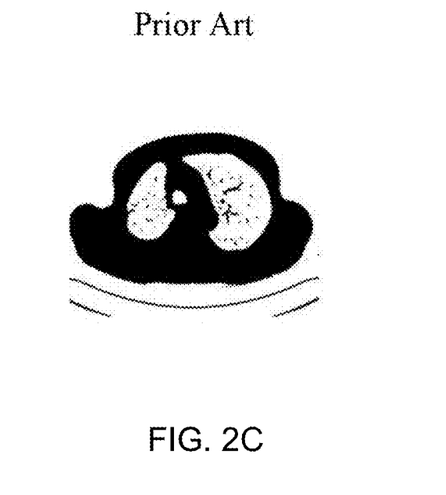
Figure 2D:
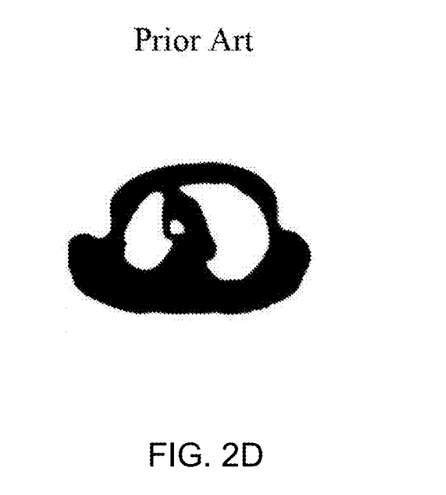
Figure 2E:
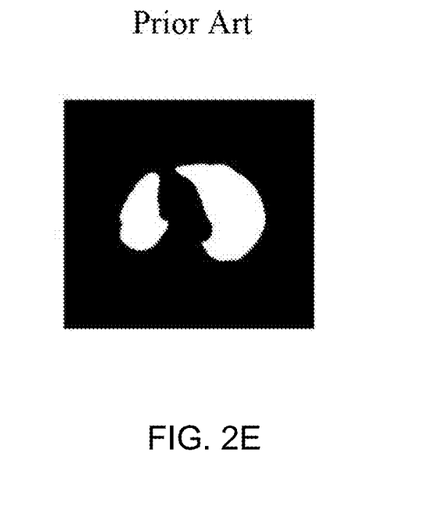

As shown, an image is converted following the flow of the step of determining a pulmonary area (S100) in an exemplary method of the pulmonary vessel extraction for automatically detecting a lesion in a thoracic CT image. In particular, FIG. 2(A) shows an original image, FIG. 2(B) shows a gamma corrected image, FIG. 2(C) shows a binary image, FIG. 2(D) shows an image following the morphological operation performed thereon, and FIG. 2(E) shows a pulmonary area thus determined, respectively.

The Otsu's method is well known as a means of finding an optimal threshold, dividing the distribution of an intensity histogram in a 2D image into two classes. In general, 90 to 100 CT images are prepared for each patient. If a 3D image is generated after determining all the thresholds for separate pulmonary areas in each image, the thresholds of respective images may not be uniform, and a target pulmonary area may be determined differently in a non-consistent way. Moreover, since the top and bottom parts of the lungs are small portions of the pulmonary area in the thoracic image, a proper threshold may not be obtained. As such, the inventors decided to create a 3D image first using all of the CT images of a patient. Then they used this 3D image data to calculate a single threshold for performing the Otsu's binarization on a target pulmonary area to be determined based on that.

Going through these steps described above, pulmonary vessels can be extracted. In step S100, a pulmonary area is detected or determined with respect to the surface of the lung, and pulmonary vessels are detected within the pulmonary area.

Pulmonary vessels and lung lobes have a very close relationship in their structures. The blood vessels coming out of the heart are divided into two sides, i.e. the left side and the right side. The blood vessels on the right side are further divided into three branch vessels, while the blood vessels on the left side are further divided into two branch vessels. These branch vessels are separated within each lung lobe portion, spreading out towards the respective lobe portions. Therefore, analyzing the distribution of pulmonary vessels requires analyzing pulmonary vessels by lobe.

SUMMARY

This section provides a general summary of the disclosure and is not a comprehensive disclosure of its full scope or all of its features.

According to one aspect of the present disclosure, there is provided a method for the quantification of pulmonary vessels by lobe, the method including extracting, at extraction unit, pulmonary vessels based on a medical image, locating, at analysis unit, voxels of pulmonary vessels with respect to the surface of a lobe, and quantifying, at calculation unit, the extracted pulmonary vessels.

These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The present disclosure will now be described in detail with reference to the accompanying drawing(s).

Figure 3A:
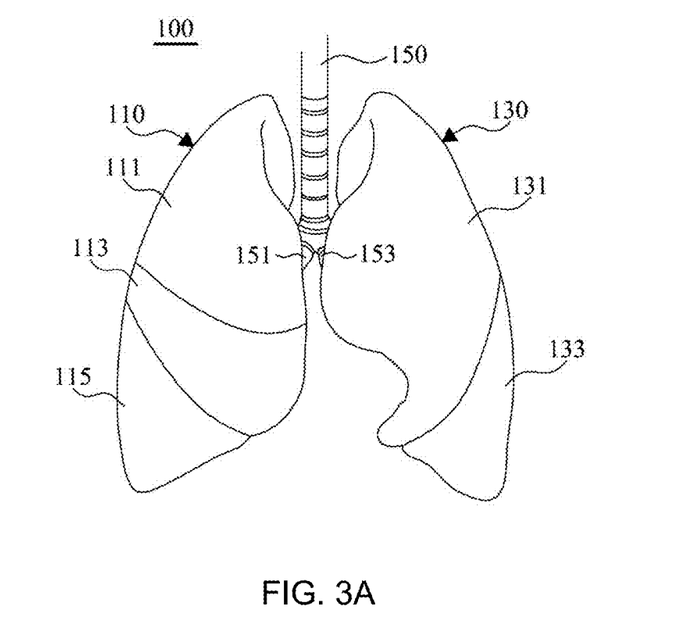
FIG. 3A and FIG. 3B illustrate a relationship between lungs and lobes.
Figure 3B:
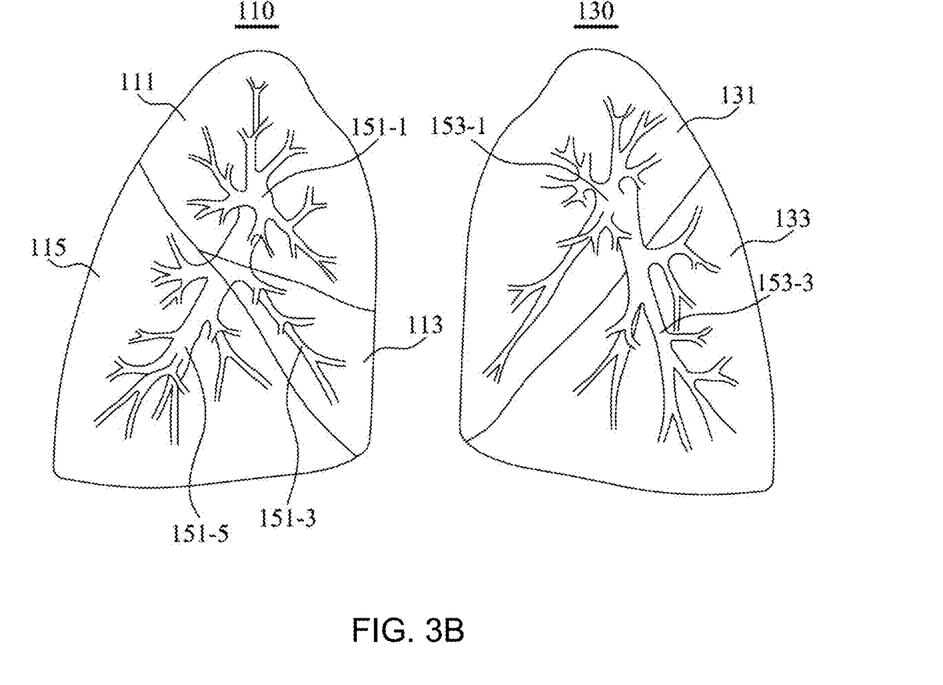

FIG. 3(A) and FIG. 3(B) illustrate a relationship between lungs and lobes;

In particular, FIG. 3(A) shows the entire lung 100, and FIG. 3(B) shows bronchi 151, 153, and the entire lung 100.

The lung 100 has a right lung 110 and a left lung 130, and a trachea 150 between the right lung 110 and the left lung 130. During inhalation, air flows into the lungs through the trachea 150; during exhalation, air flows out of the lungs. For the lung 100, the right lung 110 has three lobes (lung lobes) 111, 113, 115, and the left lung 130 has two lobes 131, 133.

Although the right lung 110 and the left lung 130 of the whole lung 100 seem to be a single mass, respectively, they are divided into five lobes 111, 113, 115, 131, 133 in total. The lobes are divided by bronchus 151, 153, and pulmonary vessels (not shown) are located around the bronchi 151 and 153. Therefore, in practice, it is accurate to extract pulmonary vessels with respect to the corresponding lobe 111, 113, 115, 131, 133, while the lobes 111, 113, 115, 131, 133 are divided by bronchus 151, 153. In addition, the lung 100 can be segmented into a greater number of lobes according to the division of pulmonary vessels or bronchi 151 and 153.

Referring to FIG. 3(B), bronchi 151-1, 151-3, 151-5, 153-1, 153-3 are also distributed to the respective lobes. In other words, the lobes can be divided by bronchus 151-1, 151-3, 151-5, 153-1, 153-3 or pulmonary vessels surrounding the corresponding bronchus 151-1, 151-3, 151-5, 153-1, 153-3.

Figure 4:
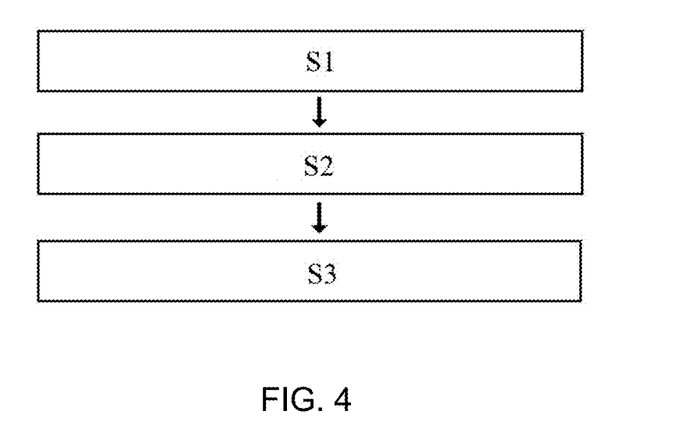
FIG. 4 is a flow chart describing a method for the quantification of pulmonary vessels by lobe.

FIG. 4 is a flow chart describing a method for the quantification of pulmonary vessels by lobe.

In the method for the quantification of pulmonary vessels by lobe, first of all, extraction unit extracts vessels based on a medical image (S1). The vessels are extracted as a 3D set of voxels based on the medical image. On the medical image, the extraction unit can locate voxels of the vessels according to a HU (Hounsfield Unit) value thereof. For instance, the extraction unit can find voxels having at least −750 HU in order to find a target vessel. This is discussed below in reference to FIG. 5.

Next, analysis unit locates voxels of pulmonary vessels with respect to the surface of a lobe (S2).

The surface of a lobe has an outer lobe face and an inner lobe face. The outer lobe face corresponds to an exterior surface of the lung, and the inner lobe face refers to an interface formed between lobes.

Figure 7A:
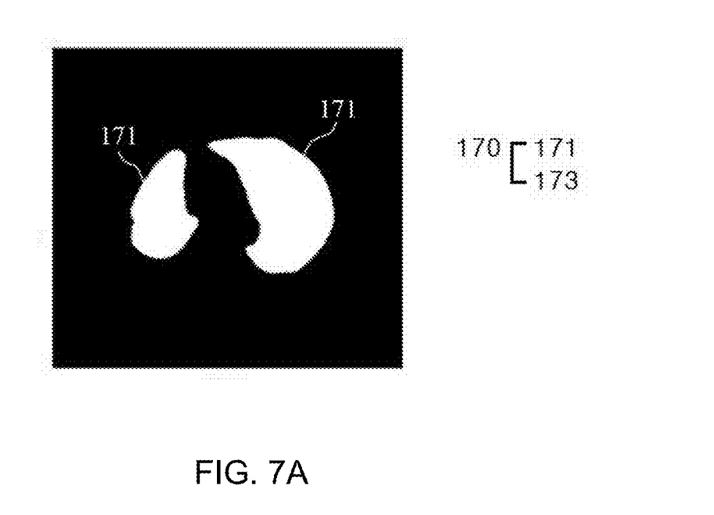
FIG. 7A and FIG. 7B describe a procedure of locating the surface of a lobe, according to the present disclosure.
Figure 7B:
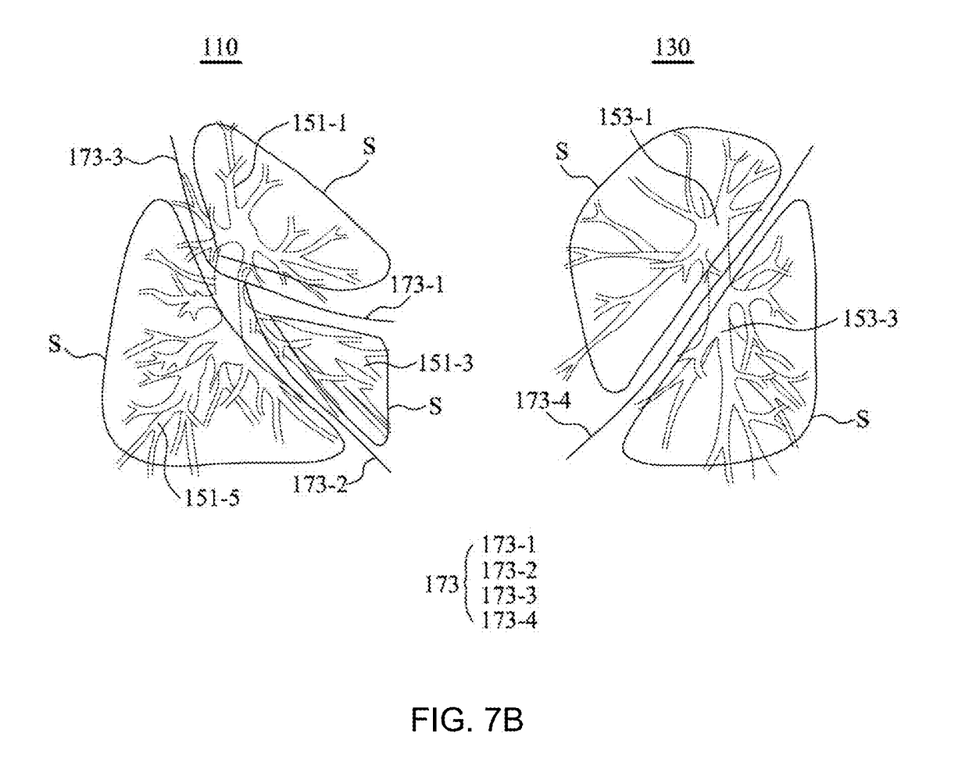

Moreover, the quantification method involves locating an outer lobe face as well as locating an inner face between lobes. Such an inner face between lobes can be predicted with respect to a bronchus or pulmonary vessel on the medical image. The medical image around this predicted inner face is then used for locating an inner face between lobes. More details on this will be provided below in reference to FIG. 7.

Figure 6A:
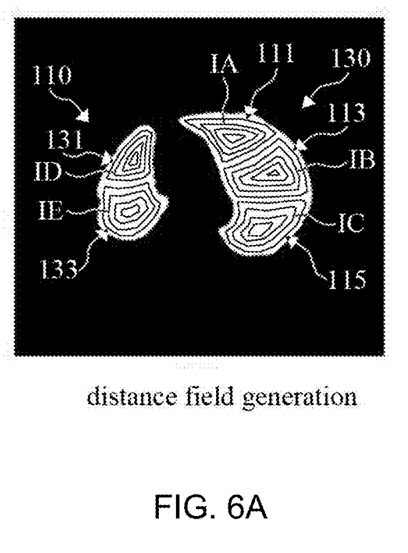
FIG. 6A and FIG. 6B describe offset surfaces according to the present disclosure.
Figure 6B:
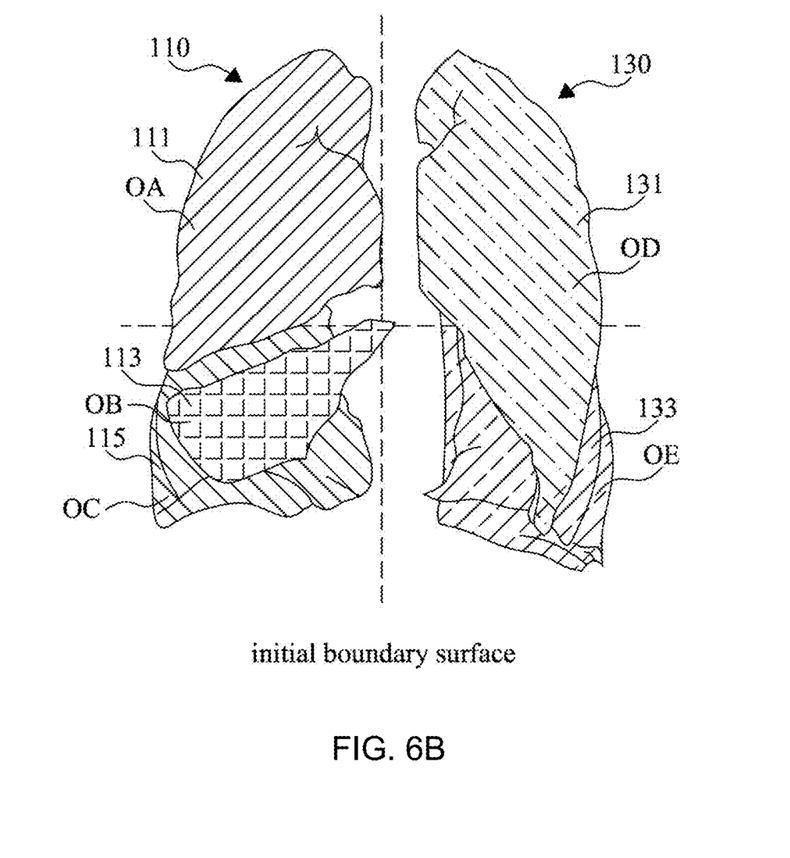

Analysis unit forms an offset surface with respect to the surface of a lobe. The term 'offset surface' is defined as a set of voxels at a predefined distance inwardly from the surface of a lobe. Further, voxels of pulmonary vessels corresponding to the intersection between the offset surface and the extracted vessel are found. More details on this will be provided below in reference to FIG. 6.

Next, calculation unit quantifies pulmonary vessels that were extracted (S3). In particular, calculation unit calculates a radial distance or diameter of pulmonary vessels using their voxels found. Moreover, calculation unit calculates an area ratio of pulmonary vessels with their radial distance thus obtained. Calculation unit may also calculate volume of the pulmonary vessels using their voxels.

Figure 5:
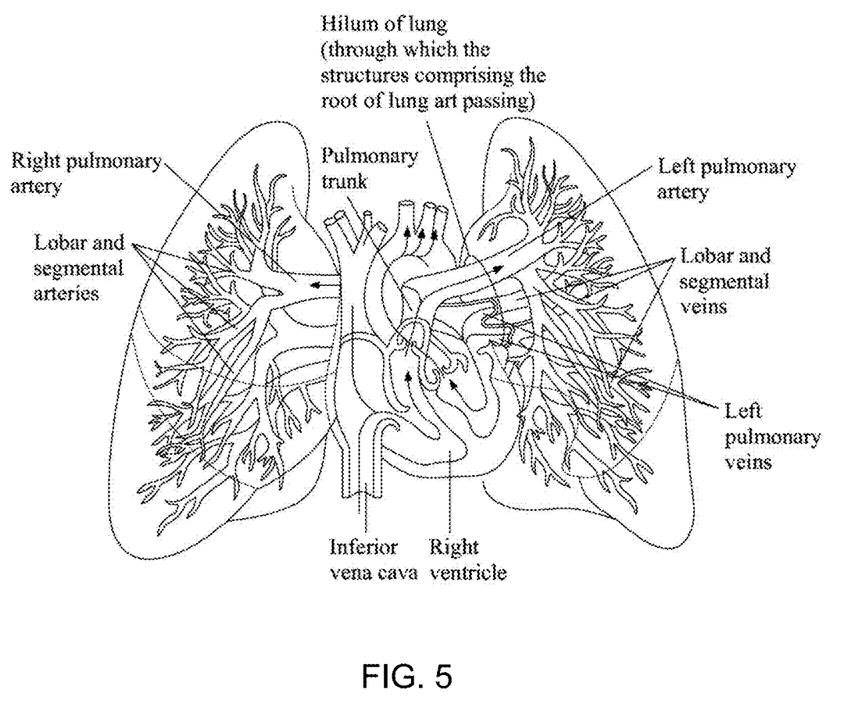
FIG. 5 shows an example of extracted vessels according to the present disclosure.

FIG. 5 shows an example of extracted vessels according to the present disclosure.

Vessel extraction is done on the medical image. In particular, all vessels shown on the medical image are extracted and put together as data, thereby constructing 3D vessels. In case of extracting blood vessels from a thoracic medical image, cardiac vessels as well as pulmonary vessels can be extracted. In FIG. 5, only blood vessels having a predefined diameter or greater are shown, and any blood vessels having a diameter shorter than the predefined diameter are not shown even if they are extracted.

FIG. 6(A) and FIG. 6(B) describe offset surfaces according to the present disclosure.

An exemplary method of generating a Euclidean Distance field to form an offset surface will now be described.

Based on a fact that pulmonary branch vessels are stretched out to an end region from the inside of the body, an assumption can be made that there would be similar sized vessels at the same distance from outer end boundary surfaces of lobes. Therefore, it is necessary to locate intersections between vessels excluding those in the mediastinal region and inner surfaces IA, IB, IC, ID, IE (hereinafter "I" (inner surface)) of the lung at a predefined distance from the outer end boundary surfaces of lobes, and to assess diameters of pulmonary vessels in those intersections.

In order to obtain such intersections, first of all, inner surfaces I should be gradually extracted. The inner surfaces I at a predefined distance from the outer end boundary surfaces of lobes become offset surfaces OA, OB, OC, OD, OE (hereinafter "O" (offset surfaces)) at that distance. Similar to face-based offset or vertex-based offset calculations, these offset surfaces O can be formed with surface data calculation schemes that are more efficient (time-wise) than volume-based calculation schemes.

However, the aforementioned surface data calculation schemes do not properly work in the presence of local and overall interferences that often occur when the surfaces of lobes are being offset inwardly. Particularly in this exemplary embodiment, offset distances range from 5 mm to 30 mm, which are much larger than lengths of a surface extracted by marching cubes from CT images, making it more difficult to avoid the interferences. Hence, in this exemplary embodiment, offset surfaces O are formed with volume-based schemes which generate a Euclidean Distance field (see FIG. 6(A)).

For instance, referring to FIG. 6(A), the lung is divided into lobes 111, 113, 115, 131, 133. The lobes 111, 113, 115, 131, 133 form at least one offset surface O inwardly from the surfaces of the lobes. Among others, an offset surface O formed inwardly of a lobe is called an inner surface I.

FIG. 6(B) illustrates offset surfaces O formed on the lobes 111, 113, 115, 131, 133, respectively.

After obtaining these inner surfaces I, i.e. offset surfaces O at a predefined distance, intersections between the offset surfaces O and small vessels are located. More details on this will be provided below in reference to FIG. 8 to FIG. 9.

FIG. 7(A) and FIG. 7(B) describe a procedure of locating the surface of a lobe, according to the present disclosure.

The surface 170 of a lobe has an outer lobe face 171 and an inner lobe face 173. For instance, the lung 100 includes a right lung 110 on the right hand side, and a left lung 130 on the left hand side. The right lung 110 has a first lobe 111 (see FIG. 3) on the upper part, a second lobe 113 (see FIG. 3) in the middle part, and a third lobe 115 (see FIG. 3) on the lower part. The left lung 130 has a fourth lobe 131 (see FIG. 3) on the upper part and a fifth lobe 133 (see FIG. 3) on the lower part. A first inner face 173-1 is present between the first lobe 111 and the second lobe 113. A second inner face 173-2 is present between the second lobe 113 and the third lobe 115. A third inner face 173-3 is present between the first lobe 111 and the third lobe 117. A fourth inner face 173-4 is present between the fourth lobe 131 and the fifth lobe 133.

First of all, the outer lobe face 171 is located. The outer lobe face 171 corresponds to the surface of the lung. Therefore, the surface of the lung is located on the medical image. For instance, once the pulmonary area is determined as in FIG. 2, it is separated from the medical image. In this sense, FIG. 7(A) may be referred to as the surface of the lung or as the outer lobe face 171.

Next, the inner lobe face 173 is located. As can be seen in FIG. 7(B), a fissure that forms an interface (hereinafter, inner face 173) between lobes on the medical image is very thin and therefore, very difficult to distinguish. For instance, ranges or scopes S are set with respect to the extracted pulmonary vessels or bronchi (151-1, 151-3, 151-5, 153-1, 153-3), and inner face 173 between the scope S is located on the medical image. Locating the inner face 173 can be done by artificial intelligence. That is, with the lobes being divided by the extracted pulmonary vessels or bronchi (151-1, 151-3, 151-5, 153-1, 153-3), it is possible to predict where the inner face 173 is possibly going to be located, based on thickness and length of the pulmonary vessels or bronchi (151-1, 151-3, 151-5, 153-1, 153-3). In this way, the scope is defined, and the inner face 173 is found.

FIG. 8(A) to (B) and FIG. 9(A) to (B) illustrate benefits of locating pulmonary vessels with respect to the surface of a lobe, according to the present disclosure.

Figure 8A:
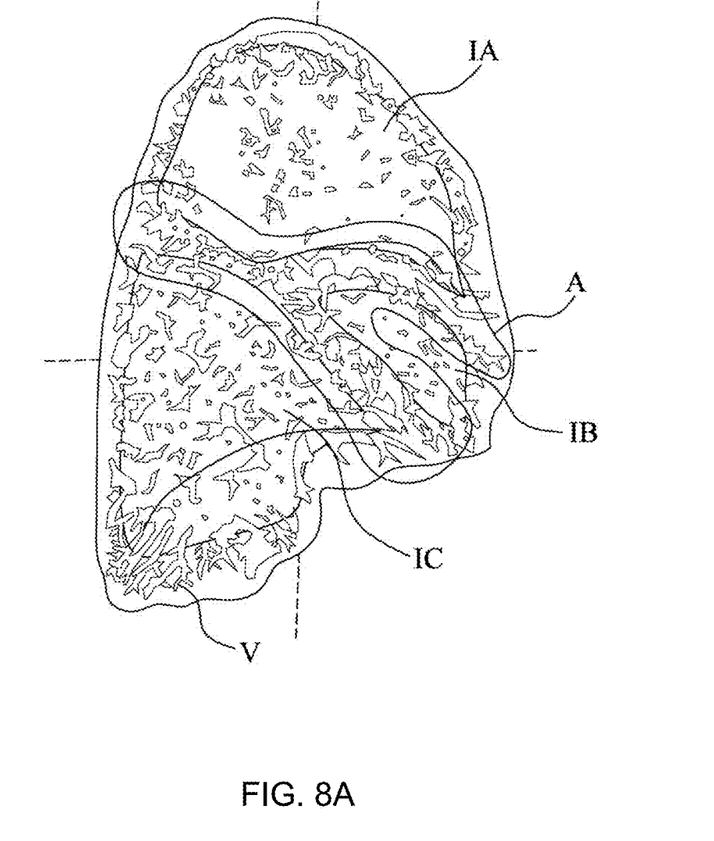
FIGS. 8A and 8B and FIGS. 9A and 9B illustrate benefits of locating pulmonary vessels with respect to the surface of a lobe, according to the present disclosure.
Figure 8B:
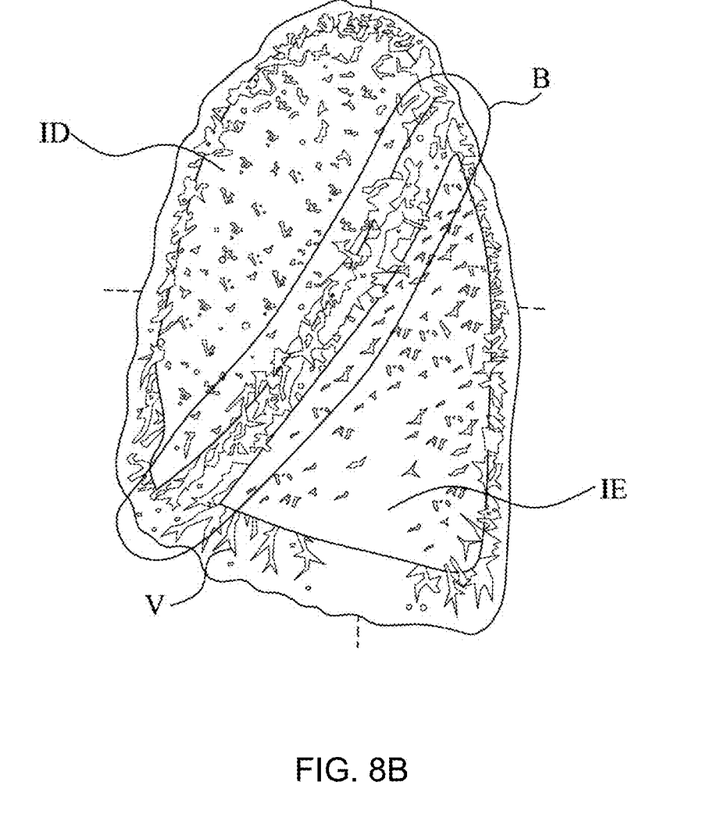
Figure 9A:
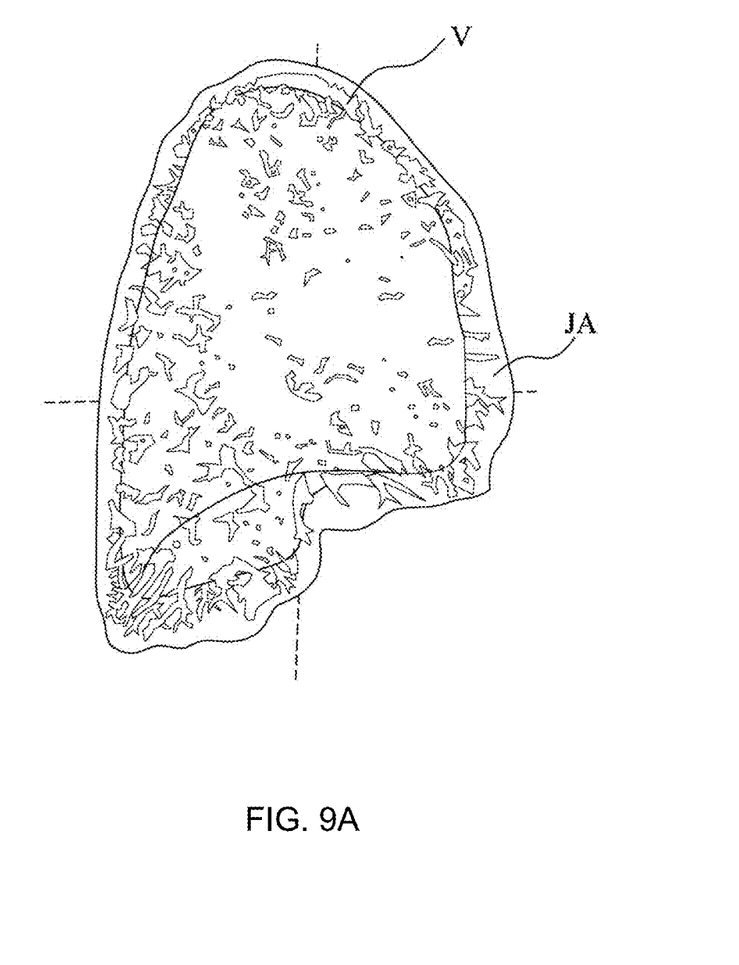
Figure 9B:
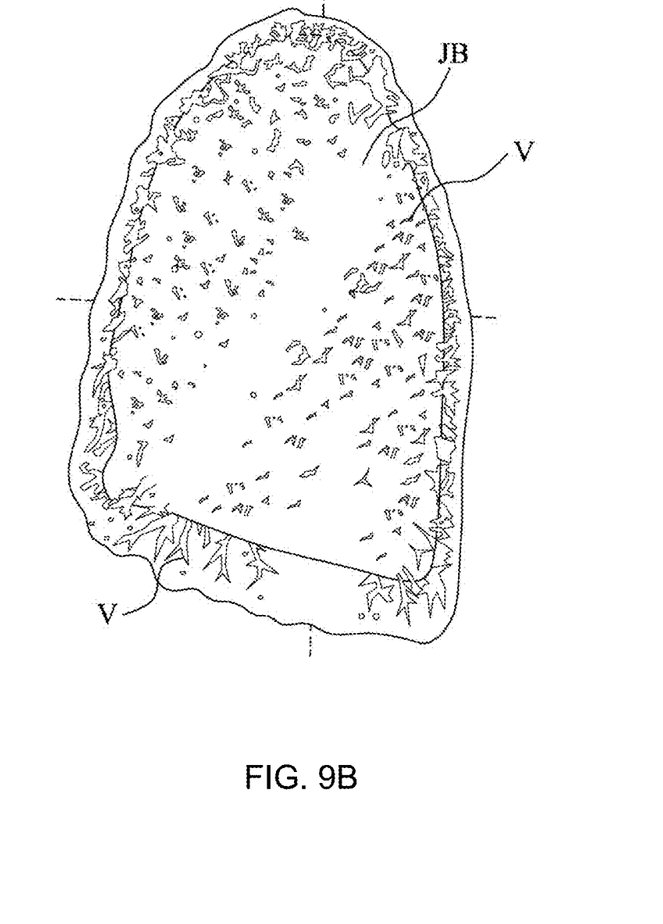

In particular, FIG. 8(A) and FIG. 8(B) each show one inner surface out of many inner surfaces with respect to the surface of a lobe, and FIG. 9(A) and FIG. 9(B) each show one inner surface out of many inner surfaces with respect to the surface of the lung.

The inner surfaces shown in FIG. 8(A) and FIG. 8(B) are formed with respect to the surface of a lobe as mentioned above, and pulmonary vessels are extracted at the intersections between these inner surfaces and the pulmonary vessels.

Similarly, the inner surfaces shown in FIG. 9(A) and FIG. 9(B) are formed with respect to the surface of the lung as mentioned above, and pulmonary vessels are extracted at the intersections between these inner surfaces and the pulmonary vessels.

Because the inner surfaces IA, IB, IC, ID, IE in FIG. 8(A) and FIG. 8(B) are formed with respect to the surface of a lobe, the distribution of pulmonary vessels V can be measured to agree with anatomical structure of real blood vessels. Meanwhile, because the inner surfaces IA, IB, IC, ID, IE in FIG. 9(A) and FIG. 9(B) are formed with respect to the surface of the lung, the distribution of pulmonary vessels V can be measured regardless of anatomical structure of real blood vessels. In other words, with the inner surfaces IA, IB, IC, ID, IE (with respect to the surface of the lung) in FIG. 9(A) and FIG. 9(B), other vessel-free areas are also included in the analysis of the distribution of pulmonary vessels, negatively affecting reliability of the analysis results.

Set out below are a series of clauses that disclose features of further aspects of the invention, which may be claims.

(1) A method for the quantification of pulmonary vessels by lobe, the method including: extracting, at extraction unit, pulmonary vessels based on a medical image; locating, at analysis unit, voxels of pulmonary vessels with respect to the surface of a lobe; and quantifying, at calculation unit, the extracted pulmonary vessels.

(2) There is also provided, the method of clause (1) wherein: locating, at analysis unit, voxels of pulmonary vessels with respect to the surface of a lobe includes forming offset surfaces at a predefined distance from the surface of a lobe.

(3) There is also provided, the method of clause (2) wherein: locating, at analysis unit, voxels of pulmonary vessels with respect to the surface of a lobe further includes, after forming offset surfaces at a predefined distance from the surface of a lobe, locating voxels that correspond to intersections between the extracted pulmonary vessels and the offset surfaces.

(4) There is also provided, the method of clause (1) wherein: locating, at analysis unit, voxels of pulmonary vessels with respect to the surface of a lobe includes locating an outer lobe face and locating an inner lobe face, with the outer lobe face and the inner lobe face comprising the surface of a lobe.

(5) There is also provided, the method of clause (4) wherein: locating an inner lobe face involves locating a first inner face, a second inner face, a third inner face and a fourth inner face, with the first inner face being present between a first lobe on the upper part of the right lung and a second lobe in the middle part of the right lung, with the second inner face being present between the second lobe and a third lobe on the lower part of the right lung, with the third inner face being present the third lobe and a fourth lobe on the upper part of the left lung, with the fourth inner face being present between the fourth lobe and a fifth lobe on the lower part of the left lung.

(6) There is also provided, the method of clause (2) wherein: in forming offset surfaces at a predefined distance from the surface of a lobe, the offset surfaces are formed inwardly from the surface of a lobe, and at least one offset surface is formed, with the offset surfaces including inner surfaces provided inside.

(7) There is also provided, the method of clause (1) wherein: the extraction unit extracts all blood vessels on the medical image.

(8) There is also provided, the method of clause (1) wherein: in extracting, at extraction unit, pulmonary vessels based on a medical image, the medical image is obtained by extracting voxels of blood vessels.

In the method for the quantification of pulmonary vessels by lobe according to an exemplary embodiment of the present disclosure, offset surfaces are formed with respect to a lobe, allowing more accurate extraction of pulmonary vessels.

In the method for the quantification of pulmonary vessels by lobe according to another exemplary embodiment of the present disclosure, the surface of a lobe is divided such that a greater number of pulmonary vessels can be located.

DRAWING REFERENCE NUMERALS

S110: Gamma correction
S120: 3D Otsu's binarization
S130: Morphology
S140: Determining pulmonary area
S210: Determining of pulmonary vascular region
S220: Thinning a vessel candidate
S230: Post-processing thinned results
S240: Smoothing thinned results
S310: Determining first topology point
S320: Constructing vascular topology
S330: Post-processing vascular topology
S340: Re-constructing vascular topology
S410: Generating unit skeleton reference points
S420: Selecting 3D model for analysis of thickness
S430: Analyzing thickness of blood vessels
S440: Re-classifying nodule candidates

What is claimed is:

1. A method for the quantification of pulmonary vessels by lobe, the method comprising:
   extracting, at extraction unit, pulmonary vessels based on a medical image;
   locating, at analysis unit, voxels of pulmonary vessels with respect to the surface of a lobe; and
   quantifying, at calculation unit, the extracted pulmonary vessels,
   wherein the locating, at the analysis unit, voxels of pulmonary vessels with respect to the surface of the lobe further comprises:
      forming at least one offset surface as a set of voxels at a predefined distance inwardly from the surface of the lobe; and
      after forming the at least one offset surface, locating voxels that correspond to intersections between the extracted pulmonary vessels and the at least one offset surface, and
   wherein the quantifying, at the calculation unit, the extracted pulmonary vessels further comprises:
      quantifying the extracted pulmonary vessels based on the intersections between the extracted pulmonary vessels and the at least one offset surface such that a distribution of pulmonary vessels is measured to correspond to an anatomical structure of pulmonary vessels.

2. The method according to claim 1, wherein locating, at analysis unit, voxels of pulmonary vessels with respect to the surface of a lobe further comprises:
   locating an outer lobe face; and
   locating an inner lobe face, with the outer lobe face and the inner lobe face comprising the surface of a lobe.

3. The method according to claim 2, wherein locating an inner lobe face involves locating a first inner face, a second inner face, a third inner face and a fourth inner face, with the first inner face being present between a first lobe on the upper part of right lung and a second lobe in the middle part of right lung, with the second inner face being present between the second lobe and a third lobe on the lower part of right lung, with the third inner face being present the third lobe and a fourth lobe on the upper part of left lung, with the fourth inner face being present between the fourth lobe and a fifth lobe on the lower part of left lung.

4. The method according to claim 1, wherein, in forming the at least one offset surface, the at least one offset surface is formed such that the at least one offset surface includes inner surface of the lobe which is provided inside the surface of the lobe.

5. The method according to claim 1, wherein the extraction unit extracts all blood vessels on the medical image.

6. The method according to claim 1, wherein, in extracting, at extraction unit, pulmonary vessels based on a medical image, the medical image is obtained by extracting voxels of blood vessels.

* * * * *